(12) United States Patent
Sheftell et al.

(10) Patent No.: US 6,194,432 B1
(45) Date of Patent: Feb. 27, 2001

(54) PREVENTION AND TREATMENT OF MIGRAINE, CLUSTER AND OTHER RECURRENT HEADACHES USING LEUKOTRIENE ANTAGONIST DRUGS

(75) Inventors: Fred D. Sheftell, 778 Long Ridge Rd., Stamford; Robert C. Kevorkian, West Granby, both of CT (US)

(73) Assignee: Fred D. Sheftell, Stamford, CT (US)

( * ) Notice: Subject to any disclaimer, the term of this patent is extended or adjusted under 35 U.S.C. 154(b) by 0 days.

(21) Appl. No.: 09/221,015

(22) Filed: Dec. 23, 1998

Related U.S. Application Data

(60) Provisional application No. 60/103,933, filed on Oct. 13, 1998.

(51) Int. Cl.$^7$ .................................................. A01N 43/42
(52) U.S. Cl. .................... 514/311; 514/312; 514/313; 514/314; 514/381; 514/443
(58) Field of Search .................... 514/311, 312, 514/313, 314, 381, 443

(56) References Cited

U.S. PATENT DOCUMENTS

| | | | |
|---|---|---|---|
| 4,602,023 | * | 7/1986 | Kiely et al. . |
| 4,775,677 | * | 10/1988 | Connor et al. . |
| 4,786,755 | * | 11/1988 | Kiely et al. . |
| 4,810,716 | * | 3/1989 | Connor et al. . |
| 4,859,692 | * | 8/1989 | Bernstein et al. . |
| 4,868,195 | * | 9/1989 | Carethers . |
| 4,868,199 | * | 9/1989 | Carethers . |
| 4,868,200 | * | 9/1989 | Carethers et al. . |
| 4,868,205 | * | 9/1989 | Carethers et al. . |
| 4,874,758 | * | 10/1989 | Carethers et al. . |
| 5,081,138 | * | 1/1992 | Gillard et al. . |
| 5,093,356 | * | 3/1992 | Girard et al. . |
| 5,102,881 | * | 4/1992 | Zamboni et al. . |
| 5,142,095 | * | 8/1992 | Connor et al. . |
| 5,190,968 | * | 3/1993 | Gillard et al. . |
| 5,204,344 | * | 4/1993 | Prasit et al. . |
| 5,221,678 | * | 6/1993 | Atkinson et al. . |
| 5,225,421 | * | 7/1993 | Gillard et al. . |
| 5,232,916 | * | 8/1993 | Zamboni . |
| 5,252,585 | * | 10/1993 | Frenette et al. . |
| 5,254,567 | * | 10/1993 | Down et al. . |
| 5,272,145 | * | 12/1993 | Prasit et al. . |
| 5,273,980 | * | 12/1993 | Frenette et al. . |
| 5,290,798 | * | 3/1994 | Gillard et al. . |
| 5,308,850 | * | 5/1994 | Gillard et al. . |
| 5,334,719 | * | 8/1994 | Frenette et al. . |
| 5,380,850 | * | 1/1995 | Prasit et al. . |
| 5,389,650 | * | 2/1995 | Frenette et al. . |
| 5,565,473 | * | 10/1996 | Belley et al. . |
| 5,629,337 | * | 5/1997 | Gray ..................................... 514/443 |
| 5,952,347 | * | 9/1999 | Arison et al. ........................ 514/311 |

OTHER PUBLICATIONS

Marx, J., "The leukotrienes in allergy and inflammation," *Science 2154*: 1380–1383 (1982).*
Denzlinger, C., et al, "Leukotrienes as mediators of tissue trauma," *Science 230*: 330332 (1985).*
Selmaj, K., et al, "Leukotriene B4 generation by polymorphonuclear leukocytes: Possible involvement in the pathogenesis of headache," *Headache 26*: 460–464 (1986).*
Gazzigna, P.P., et al, "Identification of blood leukotrienes in classical migraine," *headache 27*: 211–215 (1987).*
Parantainen, J., et al, "Clinical aspects of prostaglandins and leukotrienes in migraine," *Cephalalgia Suppl. 4*: 95–100 (1986).*
LaMancusa, R., et al, "Blood leukotriene in headache: correlation with platelet activity," *Headache 31*: 409–414 (1991).*
Prescribing information, Singulair™ (montelukast sodium) tablets (Merck & Company, Inc.) (1991).*
Prescribing information, Accolate™ (zafirlukast) tablets (Zeneca Pharmaceuticals) (1991).*

* cited by examiner

*Primary Examiner*—Frederick Krass
(74) *Attorney, Agent, or Firm*—Patrick D. Kelly

(57) ABSTRACT

A method is disclosed for using leukotriene (LT) antagonist drugs to prevent and treat recurrent primary headaches, which includes migraine headaches and cluster headaches. LT antagonist drugs (such as montelukast and zafirlukast) are commercially available, and they are safe for long-term chronic use without problems of tolerance or dependence. These drugs, taken daily in pill form, are conventionally used for treating asthma. In a clinical trial, LT antagonists taken orally each day reduced the frequency, duration, and severity of migraines, and reduced sensitivity to perfume as a triggering factor. LT antagonists were also found to increase the effectiveness of "triptan" drugs (such as sumatriptan) when used to treat acute migraine headaches.

11 Claims, No Drawings

PREVENTION AND TREATMENT OF MIGRAINE, CLUSTER AND OTHER RECURRENT HEADACHES USING LEUKOTRIENE ANTAGONIST DRUGS

RELATED APPLICATION

This application claims priority under 35 USC 119(e) based on provisional application 60/103,933, filed on Oct. 13, 1998.

BACKGROUND OF THE INVENTION

This invention is in the field of pharmacology, and relates to drugs that can help reduce the frequency, duration, and/or severity of certain types of headaches that are classified as "recurrent primary headaches", including migraine headaches and cluster headaches. The treatment disclosed herein involves daily or other chronic administration of "leukotriene antagonist" drugs, which previously have been used for treating asthma.

As is well-known, migraine headaches (also referred to simply as migraines, for convenience) are severe types of headaches. Typically, migraines are distinguished from ordinary headaches by several factors. Migraines with aura (referred to in the past as "classic" migraines) affect approximately 20% of migraine sufferers, and are usually preceded or accompanied by some type of visual, sensory or motor disturbance, known as an aura. Migraines without aura (previously known as "common" migraines) usually affect one side of head only, last between 4 and 72 hours, and are usually accompanied by nausea, vomiting, or similar symptoms. To establish a diagnosis of migraine without aura, there must have been at least 5 previous episodes; organic factors which may mimic migraine must have been ruled out; and, the attack must last 4 to 72 hours.

"Cluster headaches" were given that name because they tend to occur in episodic clusters, with a cluster cycle usually lasting 4 to 8 weeks. In some patients, a cluster occurs only once in a lifetime; in other patients, a cluster may occur roughly once a year, pith periods of complete remission between attacks; and, in the roughly 10% of patients who are chronic sufferers, there are no significant periods of remission. As opposed to migraines (which occur in women at roughly 3 times the rates as in men), cluster headaches are more prevalent in men than in women, by a factor of about 5:1 or higher.

In cluster headaches, the rain is almost always one-sided, and typically involves the eye and temple region. As opposed to migraine, which may he a throbbing type of pain, the pain of a cluster headache is almost always non-throbbing, and is often likened by the patient to a red hot poker being driven into the affected eye, with immense force. Attacks generally last about 45 to 90 minutes, and may occur several times a day. They also fairly often awaken a sufferer from sleep, when in cycle. Symptoms accompanying such attacks generally include a red and tearing eye, stuffed and running nostril, and drooping of the eyelid, all on the side of the attack. As opposed to migraine patients, who must retreat to a dark and quiet environment, the pain of cluster headaches is usually so intense that the sufferer often paces, rocks, walks about, or does anything else that may help distract him from the pain (including, in many cases, banging his head or fists against the wall, ground, or other object).

Migraines and cluster headaches are both important, well-known, and extensively studied medical problem. In many cases, they completely incapacitate a sufferer for the duration of the headache. Their physiological aspects, causative and aggravating factors, and current Treatments are discussed in detail in numerous scientific articles, and in full-length medical textbooks such as *Headache in Clinical Practice* (edited by S. Silberstein et al., Oxford Univ. Press, 1998); *The Headaches*, by J. Olesen; and *Headache Disorders: A Management Guide for Practitioners*, by A. Rapoport and F. Sheftell (W. B. Saunders, Philadelphia, 1996). In addition, various definitions, categories, and diagnostic standards are defined by standardized criteria that have been approved and issued by the International Headache Society (IHS), which were published as a supplement to the journal *Cephalalgia* in 1988.

Migraines and cluster headaches are both classified as "recurrent primary headaches". They are recurrent, since they recur with sufficient frequency to seriously interfere with the health and quality of life of a patient, to a point of requiring and demanding medical attention, as opposed to just taking aspirin or similar over-the-counter analgesics and lying down till it passes. They are also regarded as "primary" headaches, since they usually arise as a primary adverse biologic condition, independently of other causative medical conditions such as tumors, sinus or other infections, bleeding problems, etc.

A third major category of recurrent primary headaches is often referred to as "tension" (or "tension-type") headaches. Although these can often be resolved in many patients if the source of the tension can somehow be eliminated or substantially lessened, that approach may require a major lifestyle change for the patient, and is often impractical or impossible for patients who cannot escape from the demands imposed by stressful work, family, or other situations. Accordingly, recurrent tension headaches must often be treated as a medical problem using drug intervention, usually in combination with training in relaxation and stress management techniques. In addition, many researchers and physicians believe that tension headaches and migraine headaches exist on a continuum, and involve the same or overlapping neurobiological mechanisms. It should also be noted that various drugs (including anti-inflammatory drugs, such as certain types of prostaglandin antagonists) that are effective (in at least some patients) in treating migraine headaches are also effective in treating tension headaches as well. Because of their similarities and overlapping factors, it is believed by the Applicant that tension headaches may be susceptible to effective treatment, in at least some sufferers, using leukotriene antagonist drugs as disclosed herein.

There are at least three "aspects" or "traits" of primary recurrent headaches that are important in this invention, since these traits can provide quantifiable evidence of whether a treatment is or is not effective in controlling such headaches. Those three aspects are: (1) frequency, which is usually evaluated over a span of time, such as number of such headaches per week, per month, or per year; (2) duration, which evaluates (usually in hours) how long a headache lasts, from the time it begins to develop into a migraine or cluster headache, until it has been resolved; and, (3) severity (also referred to as intensity), which is based on subjective estimates of the severity or intensity of pain or other side effects (such as nausea) being suffered by patients during such headaches.

If a preventive drug treatment can significantly reduce any one of these three aspects (frequency, duration, or severity), even if it has no noticeable effects on the other two aspects, then the preventive treatment can and should be regarded as effective, successful, and beneficial to patients, since that treatment can substantially improve the quality of life for such patients.

For obvious reasons, an ideal preventive treatment would reduce all three aspects; and, indeed, the preventive treatment disclosed herein does indeed appear to accomplish that ideal goal, in at least some patients, based on an initial open-label trial. However, it must be noted that simultaneously reducing all threes aspects of headaches is not essential to providing useful and effective relief from severe headaches. A treatment which can reduce any one (or two) of those goals is effective and useful from a medical perspective, and will be enthusiastically welcomed by sufferers of migraine and/or cluster headaches (and by their families and friends).

Migraines are more common than cluster headaches, and have been studied more extensively. In addition, a better and more effective set of drugs have been developed to treat migraines, than cluster headache. For those reasons, the discussion below focuses mainly on migraines, rather than cluster headaches. However, because of various physiological and pharmacological factors, and because of the highly positive results observed so far in initial tests on migraine sufferers, it is believed by the Applicant that chronic treatment with leukotriene antagonist drugs, as disclosed herein, is also likely to provide significant benefits to at least some patients who suffer from cluster headaches, or from other types of recurrent primary headaches that do not respond adequately to other previously-known treatments.

Physiology of Migraines; Triptan Drugs

The factors that trigger or aggravate migraines vary widely among different patients. In some patients, for example, migraines are triggered by eating certain foods, such as chocolate, red wine, MSG, artificial sweeteners, or various types of aged cheese; in some patients, migraines can be triggered by perfumes or other compounds that generate odors; and in women, migraines often accompany menstruation.

Regardless of which factors trigger or aggravate migraines in any specific patient, migraine is ultimately believed to be a neurobiological disorder, with familial and genetic factors. It is believed that most cases involve a cascade of events beginning in the cortex region of the brain, with electrical changes possibly related to a phenomenon known as Cortical Spreading Depression (CSD), and cascading down to structures in the brainstem (most notably the Raphe Nuclei) which are rich in serotonergic projections. The hypothalamus and trigeminal caudate nucleus (the main relay station for head pain, located in the lower brainstem) are also involved. As a result of this process, the trigeminal vascular system is activated, causing vasodilataion and inflammation of small arteries that penetrate the dura mater. As a result of vasodilatation and what is known as "neurogenic inflammation", inflammatory and pain mediators are secreted (including Substance P, various kinins, histamine, and "calcitonin gene related peptide"), sending pain signals to the thalamus and on to the cortex. Thus, changes in blood vessels are believed to be manifested as a final common pathway, from a complex cascade of events that begin in he cortex and involve numerous structures, pathways, aid neurotransmitters in the brain.

It should also be recognizes that the pathophysiology of migraines involves both central nervous system (CNS) and peripheral pathways. The peripheral pathways involve blood vessels, as described above, while the CNS pathways involve the cortex, and brainstem structures such as the Raphe Nuclei and the trigeminal caudate nucleus.

Drug treatments for migraine headaches have improved substantially during the past few years, with the widespread introduction and use of drugs known as the "triptans". These include sumatriptan (sold under tradenames such as Imitrex and Imigran by Glaxo-Wellcome, and also used to treat cluster headaches), naratriptan (sold under the tradenames Amerge and Naramig, also by Glaxo-Wellcome), zolmitriptan (sold under the name Zomig, by Zeneca Pharmaceuticals), and rizatriptan (sold under the name Maxalt, by Merck). All of these are available as tablets for oral ingestion; in addition, for patients who suffer from nausea, several of these drugs are also available in other forms, such as subcutaneous injectable formulations, nasal sprays, and wafers or trochas designed to dissolve in the mouth.

The primary mode of action of all of these "triptan" drugs is believed to involve selective activation of certain serotonin receptors subtypes, primarily 5HT-1B receptors (which are present on blood vessels) and 5HT-1D receptors (which are present on nerve cell terminals, both peripherally and in the CNS).

Serotonin is the common name for 5-hydroxytryptan, abbreviated as 5-HT. In the CNS, 5-HT is a neurotransmitter molecule, which is generally inhibitory, since it suppresses (rather than activates) nerve signals in neurons. In vascular tissue, sumatriptan and other "triptan" drugs generally cause constriction of blood vessels in the cerebral region, and help to reverse neurogenic inflammation around those blood vessels during migraine attacks.

Lack of Effective Preventive Treatments

In general, the triptan drugs (and other therapies that are suited for acute treatment of migraines) cannot be used as preventive strategies, for a number of reasons. Two of the primary reasons are: (1) standard preventive pharmacologic treatment (involving analgesics such as aspirin and ibuprofen, ergotamine and its derivatives, etc.) simply does not work in the large majority of migraine patients; and (2) chronic administration of acute therapy (such as the triptan drugs) to migraine patients often drives a patient into a state where the patient suffers "rebound" headaches and/or chronic headaches. Indeed, chronic administration of triptan drugs has been observed to generate "transformed" migraine headaches which occur daily, as discussed in *Neurologic Clinics: Advances in Headache* (N. T. Mathew, editor; W. B. Saunders, Philadelphia, Pa., 1997).

In addition, triptan drugs can pose a risk of adverse cardiovascular events, such as heart attack, stroke, etc., so they are contraindicated in patients suffering from heart disease, stroke, uncontrolled hypertension, basilar or hemiplegic migraine, and in people who are taking various other drugs, such as monoamine oxidase inhibitors. Accordingly, before triptan drugs can be prescribed safely, the diagnosing physician must do a risk factor analysis for various potential cardiovascular disorders, especially among patients who may be overweight who smoke, or who suffer from high cholesterol, inadequate exercise levels, hypertension, a family history of heart disease or stroke, etc. Clearly, the risks involved in any such analysis would increase substantially if a doctor or patient were tempted to use triptan drugs as a chronic treatment.

In addition, toxicity syndromes may result, e.g. ulcers, other gastrointestinal bleeding, and "8th nerve" toxicity when aspirin is used chronically, hepitotoxicity if acetaminophen is use chronically, and various types of kidney damage (it has been estimated that 10% of all end-stage kidney disease is secondary to the overuse of over-the-counter non-steroidal medications). Addiction also may occur with prescription pain-killers such as butalbital products (Fiorinal, Fioricet, Esgic, etc.) or opiates (Percocet, Percodan, Codeine, Stadol, etc.). Most efforts at chronic preventive treatment also result in undesired side effects, such as fatigue, decreased energy, depression, weight gain, decreased libido, dry mouth, cardiac arrhythmias, hair loss, tremors, hepatotoxicity, etc. Most do not maintain their efficacy over sustained periods of time, and a number of such therapies require periodic monitoring of blood (including complete blood count (CBC), platelet counts, blood urea nitrogen levels, creatinine, and cholesterol levels), as well as tests to ensure that liver and/or kidney functioning has not been impaired.

In view of the important advances and options offered by the recent development of triptan drugs, it is widely agreed among headache specialists that preventive therapies have not kept pace with advances in acute therapy. All of the preventive strategies are associated with potentially serious limitations, adverse events, and side effects, all of which makes their use unattractive to doctors and patients. Even when a preventive therapy is deemed to be suitable for testing in a specific patient, the results usually show, at best, only about a 50% decrease in frequency and intensity, in about half of the patients tested on such treatment regimens.

In general, the best preventive approach that treating physicians can take under the prior art involves efforts to control any potential triggering factors (such as careful screening of the patient's diet and environment to identify triggering factors, so the patient can take extra precautions to avoid them), and treatment of any concomitant medical problems that may help trigger migraines. For example, anti-depressants are often prescribed for patients whose migraines appear to be triggered or aggravated by depression, and beta-blockers (which help regulate heartbeat rates) are prescribed for patients whose migraines appear to be triggered by fluctuations in blood pressure or heartbeat. Beta-blockers are the most commonly prescribed treatment that might be regarded as a preventive treatment for migraine. However, beta-blockers are contraindicated in patients with asthma, and there is a high correlation between asthma and migraines; roughly 20% of asthmatic patients suffer from migraines.

For various similar reasons, there also are no truly effective strategies for preventing cluster headaches.

In summary, there is a severe and very serious lack of effective and adequate preventive treatments, to reduce the frequency, duration, and/or severity of migraine or cluster headaches. Accordingly, there is a major medical need for effective preventive drug treatments that can be used in a chronic and long-term manner to prevent migraine or cluster headaches (rather than just for treating them once they have commenced), and to reduce their duration and severity when they do arise.

In addition, there is also in important medical need for improved drug treatments that can decrease the amount of pain and suffering caused by migraine or cluster headaches, once they begin. One such form of treatment would involve administration of a drug that can help reduce migraine symptoms in patients who are not adequately helped by the triptan class of drugs. Another such treatment would involve coadministration of two completely different types of drugs, which would work by completely different and independent mechanisms, to provide better pain relief than either class of drug can provide by itself.

Background Information on Leukotrienes

The subject invention involves drugs that act as "leukotriene antagonists". To the best of the Applicant's knowledge and belief, these drugs have never previously been used to treat or prevent migraine headaches or cluster headaches; instead, they are used to treat asthma. However, they have become of interest herein, and the activities of various subclasses of leukotrienes have been known since the early 1980's; also, various leukotriene antagonist drugs are known and available. Accordingly, this section provides background information on leukotrienes, and on drugs that are used to reduce leukotriene activity in asthma patients.

Leukotrienes are naturally-occurring molecules that function as inter-cellular messengers in mammals. There are several subtypes, referred to by designations such as $LTA_4$, $LTB_4$, $LTC_4$, $LTD_4$, and $LTE_4$, as discussed below.

All of these subtypes are formed from arachidonic acid, a molecule containing 20 carbon atoms, which has four internal double bonds near the center of the chain and a carboxylic acid group at one end. Arachidoric acid is continuously synthesized at cell membranes, by cleavage of certain types of phospholipids. This cleavage reaction is catalyzed by phospholipase enzymes. The free arachidonic acid is then converted into any of four different types of compounds, which are leukotrienes, prostaglandins, prostacyclins, and thromboxanes. All four of these types of compounds are called "eicosanoids".

Prostaglandins, prostacyclins, and thromboxanes all contain cyclic structures, and are created when "cyclooxygenase" enzymes (often abbreviated as COX enzymes) generate these cyclic structures from the carbon chain in arachidonic acid. Recently developed "COX inhibitor" drugs are approaching public use and sale; these apparently can inhibit certain types of pain (including arthritis pain) that cannot be treated adequately with previously known drugs.

By contrast, leukotrienes are created by the action of different types of enzymes. Initially, one of the four double bonds in arachidonic acid is converted into an epoxide structure; the three double bonds that remain give leukotrienes the "tri-ene"classification. The epoxide structure in $LTA_4$ is relatively reactive and unstable, so $LTA_4$ serves mainly as a precursor during synthesis of the other leukotrienes. $LTB_4$ is generated ashen the epoxide form is been hydrolyzed into a di-hydroxy compound, while $LTC_4$, $LTD_4$ and $LTE_4$ are all modified by the addition of cysteine, an amino acid that contains a relatively reactive sulfhydryl group (—SH) at the end of a spacer chain.

All of the eicosanoid compounds tend to aggravate inflammatory, pain, and fever responses, and they have been the targets of extensive research on anti-inflammatory and analgesic drugs. For example, anti-inflammatory steroids such as cortisone function by suppressing the phospholipase enzymes that generate arachidonic acid from membrane phospholipids. Pain-killers such as aspirin and ibuprofen act by blocking (to some extent) the cyclooxygenase enzymes that control the conversion of arachidonic acid to prostaglandins, prostacyclins, and thromboxanes.

Leukotrienes have been recognized as inflammatory agents since the early 1980's. Articles that focus on the specific cellular activities of the various leukotrienes include Smith et al 1980, Ford-Hutchison et al 1980, Bray et al 1981, Lewis 1981, Gimbrone et al 1984, and Levine et al 1984 (complete citations to articles are provided below). Review articles from that period include Bray 1993 and Piper 1984.

In the 1990's, various drug; known as "leukotriene antagonists" were identified, which can suppress and inhibit the activity of leukotrienes in the body.

The term "leukotriene antagonist" is used herein in the conventional medical sense, to refer to a drug that suppresses, blocks, or otherwise reduces or opposes the concentration, activity, or effects of one or more subtypes of naturally occurring leukotrienes. In laymen's terms, LT antagonists can be referred to as LT blockers.

LT antagonist drugs can wore by any of at least three distinct mechanisms: (i) by inhibiting the enzymes that convert arachidonic acid into leukotrienes; (ii) by competitively occupying leukotriene receptors on the surfaces of cells, thereby making those receptors unavailable to react with leukotrienes, without triggering ("agonizing") the cellular reactions that are triggered by leukotrienes; or (iii) by binding to leukotriene molecules in blood or other body fluids, thereby entangling or altering the leukotriene molecules and rendering them unable to trigger leukotriene receptors.

Two leukotriene (LT) antagonist drugs have become successful and widely used treatments for asthma, since they can help suppress the bronchial and alveolar constrictions that cause or aggravate asthma attacks. Those two drugs are: (i) zafirlukast, which is sold under the tradename "Accolate" by Zeneca Pharmaceuticals (Wilmington, Del.), and (ii) montelukast, sold under the tradenames "Singulair" by Merck and Company (West Point, Pa.). Various other LT antagonist drugs are also known, such as pranlukast (discussed in Hamilton et al. 1998), BAYx7195 (discussed in Boulet et al. 1997), LY293111 (discussed in Evans et al. 1996), ICI 204,219 (discussed in Taylor et al. 1991, Dahlen et al. 1991, and other articles), and ONO-1078 (discussed in Taniguchi et al. 1993). All of these LT antagonist drugs listed above are believed to help control and suppress asthma attacks primarily by competitive binding to (and blocking of) one or more types of leukotriene receptors on bronchial cells and various types of blood cells.

In addition, various drugs are known which can inhibit the synthesis of LT molecules, by inhibiting one or more of the lipoxygenase enzymes that synthesize LT molecules. Such drugs include BAYx1005 (discussed in Hamilton et al. 1997 and Dahlen et al. 1997), MK-886 (discussed in Friedman et al. 1993), MK-0591 (discussed in Diamant et al. 1995), ZD2138 (discussed in Nasser et al. 1994), and zileuton (also known as A-64077, discussed in Hui et al. 1991 and in Knapp 1990).

The effects of these drugs on asthma sufferers are discussed in various articles such as Busse 1996 (a review article) and other articles cited therein, and in a number of articles published after that review, such as Evans et al. 1996, Roquet et al. 1997, Boulet et al. 1997, Dahlen et al. 1997, and Hamilton et al. 1997 and 1998.

Accolate and Singulair are both sold in pill form, and can be taken every day for long periods of time. Rather than creating tolerance or dependence problems, these drugs appear to help suppress and reduce ongoing asthma problems, when taken chronically, by helping suppress the hypersensitive immune or allergic responses that often grow cumulatively worse in people who suffer from unwanted and excessive activity of the allergic or other immune systems.

As noted above, leukotriene antagonists have not previously been used to treat or prevent migraine or cluster headaches. Instead, there is a major medical need for a treatment that can be used on a chronic and long-term basis, to prevent migraine and/or cluster headaches. This is a very serious, important, and unmet medical need; the seriousness and importance of this unmet need have been known for decades, by the millions of people who suffer from the intense pain of severe and debilitating migraine headaches, and by the thousands of physicians and researchers who have been looking for decades for such a treatment without success.

Accordingly, one object of the subject invention is to disclose and provide a method for long-term and chronic yet safe administration of a drug that can prevent migraine or cluster headaches, and which can reduce their frequency in a patient who suffers from such headaches.

Another object of this invention is to disclose and provide a method for long-term and chronic administration of a drug that can reduce the duration and/or severity of migraine or cluster headaches, when they do arise.

Another object of this invention is to disclose and provide a method for treating migraine headaches among patients who are not adequately and effectively treated by "triptan" drugs such as sumatriptan, naratriptan, zolmitriptan, and rizatriptan.

Yet another object of this invention is to disclose and provide a method for coadministering two different types of drugs, which work by completely different and independent mechanisms, to provide better pair relief for migraine and cluster headaches than either drug can provide by itself.

These and other objects of the invention will become more apparent through the following summary and description of the preferred embodiments.

SUMMARY OF THE INVENTION

A method is disclosed for using leukotriene (LT) antagonist drugs to prevent and treat certain types of severe headaches, referred to herein as "recurrent primary headaches", which includes migraine headaches and cluster headaches. Various drugs that act as LT antagonists are commercially available, including montelukast and zafirlukast. These drugs are conventionally used for treating asthma, typically in the form of pills that are taken once or twice per day, and they have been show to be safe for long-term and chronic use in such manner, without problems of tolerance and/or dependence.

It has recently been discovered that, in at least some patients who suffer from migraine headaches, LT antagonist drugs apparently can reduce the frequency, duration, and/or severity of their headaches, even in patients who did not respond adequately to any previously known medical treatment. Accordingly, LT antagonist drugs appear to be able to provide an important and highly useful medical treatment, to reduce the frequency, duration, and/or severity of migraine headaches, and possibly cluster headaches and other types of recurrent primary headaches, using dosage forms such as pills that can be taken every day, with no tolerance, dependence, or other adverse effects.

Because of their modes of action, which involve suppressing certain types of inflammatory activities mediated by blood cells, it is also believed that LT antagonists can also be used as "acute" treatments, to help treat migraine or cluster headaches that have already arisen. In this type of treatment, they can be used (i) in combination with the "triptan" class of drugs, such as sumatriptan, naratriptan, zolmitriptan, and rizatriptan; ii) in patients who do not respond adequately to triptan drugs, and who need alternate forms of treatment for migraine;; and (iii) as substitutes or alternatives for triptan drugs, to avoid their overuse among patients who suffer from frequent migraines.

DESCRIPTION OF THE PREFERRED EMBODIMENTS

This invention relates to the use of drugs known as "leukotriene antagonists", for preventing or treating migraine or cluster headaches. Various LT antagonist drugs are known, and have been used in the past for treating asthma patients. As noted above, the two most widely used leukotriene antagonists are (i) zafirlukast, which is sold under the tradename "Accolate", and (ii) montelukast, sold under the tradename "Singulair". Both of these are used for treating asthma patients, and have never previously been used for chronic treatment (or any other treatment) to prevent migraine or cluster headaches. Other LT antagonist drugs have also been reported in the literature (citations are provided above), which fall generally into two categories: (1) LT receptor-blocking drugs, such as pranlukest, BAYx7195, LY293111, ICI 204,219, and ONO-1078; and, (2) drugs which inhibit the biosynthesis of leukotrienes, such as BAYx1005, MK-886, MK0591, ZD2138, and zileuton. Any of these LT antagonist drugs, and any other LT antagonist drugs discovered in the future, can be tested for use as described herein, using no more than routine experimentation.

Initial results which were gathered in an "open-label" trial, described below, strongly indicate that these drugs are effective in reducing the frequency, duration, and/or severity of migraine headaches, among at least some patients who are susceptible to such headaches.

This invention and application do not claim or assert that all patients who suffer from migraine or cluster headaches will benefit from LT antagonist treatment. Nevertheless, this invention discloses that at least some such patients will benefit substantially from daily or other chronic administration of one or more LT antagonist drugs. Such treatment can reduce, in at least some patients, at least one and usually two (or even all three) of the three main quantifiable traits of recurrent severe headaches (i.e., the frequency, duration, and/or severity of such headaches).

In one preferred embodiment an LT antagonist drug is administered in oral form (either a "unit dosage" form with a pre-determined quantity of the drug, such as a tablet, capsule, or other pill; other oral forms, such as syrups, can also be used if desired), at a suitable dosage rate (such as one or two pills per day), on a chronic and long-term basis (such as for months at a time). When administered in such manner, an LT antagonist drug can help prevent and/or reduce the frequency of migraine and/or cluster headaches, and can help reduce the duration and/or severity of such headaches if and when they do occur.

As used herein, terms such as "preventing" and/or "treating" headaches are used broadly. "Preventing" headaches refers to a treatment which reduces the occurrence or frequency of migraine or cluster headaches (which typically can be expressed in terms such as the average number of headaches per month or per year). "Treating" headaches is a broader term, and includes a drug treatment that can effectively reduce the frequency of such headaches, the duration of such headaches, or the severity of such headaches (which includes a reduction in pain intensity, a reduction in side effects such as nausea, and other such effects that would be regarded as beneficial by a migraine sufferer). As used herein, "treating" migraine or cluster headaches using LT antagonist drugs also refers to a method of using LT antagonist drugs to increase that potency or efficacy of one or more other drugs (such as aspirin, acetaminophen, ibuprofen, naproxen, sumatriptan, ergotamine, or other analgesics) in treating migraine or cluster headaches if and when such headaches occur.

As used herein, all references to "headache" refer to migraine headaches and/or cluster headaches, as those terms are commonly used and interpreted by physicians who specialize in treating such headaches. It is recognized by the Applicants that treatment using LT antagonist drugs may be able to also help reduce the frequency or severity of other types of headaches as well (especially including severe recurrent headaches, such as tension headaches, which for one reason or another are not classified as migraine or cluster headaches). However, this current patent application does not cover or claim the use of LT antagonists as a general treatment for any and all types of headaches.

Instead, this current application is (1) limited to the use of LT antagonists as treatment agents for reducing the frequency, duration, and/or severity of "recurrent primary headaches" (which especially includes migraine and cluster headaches), since there is a major and pressing need for such treatment. Prior to this discovery, there have been no adequate drug treatments that can accomplish those goals in treating either migraine or cluster headaches. A new drug treatment that can achieve those results would be an extraordinary blessing and benefit, for the millions of people who suffer from severe and after debilitating migraine and/or cluster headaches.

One of the primary advantages of using LT antagonist drugs on a chronic basis to hell prevent migraine headaches is that such drugs apparently do not create any problems of tolerance or dependency. Instead, these drugs appear to help suppress, control, and reduce, over the long term, the gradually cumulative problems that characterize hypersensitive immunological activity, in which a patient's immune or allergic system keeps getting primed, sensitized, triggered, or otherwise perturbed in ways which disrupt its desired "stand-by" status, and which generate repeated episodes of unwanted activity, inflammation, and other problems. Accordingly, LT antagonists appear to offer an ideal approach to a long-term preventive ("prophylactic") treatment to reduce the number of episodes of acute migraine or cluster headaches, and to reduce the number of "early onset" episodes which indicate the approach of a migraine or cluster headache in ways that require immediate medical intervention, using sumatriptan or other powerful analgesics, to prevent or reduce the onset or severity of a full-blown acute attack.

Short-Term Treatment For Emergency Headaches

In another preferred embodiment, LT antagonists can also be used for short-term treatment of a migraine and/or cluster headache that has already commented, either during the early-onset stage, or after it has became a full-blown acute headache.

In this mode of treatment, an LT antagonist can be administered on its own, or in conjunction with any other type of analgesic (such as aspirin, acetaminophen, ibuprofen, or naproxen) or acute migraine treatment (such as ergotamine or a triptan drug). It is believed that, by helping reduce and suppress leukotrienes (which are naturally occurring etiologic agents that can aggravate and possibly even trigger migraine or cluster headaches), LT antagonists can provide a form of treatment which can act in an additive and possibly synergistic manner, to increase and improve the efficacy, speed, and other beneficial results of other types of analgesic drugs that are used to treat migraine or cluster headaches.

In addition, it is believe that LT antagonists may be able to offer substantial pain relief and other benefits to migraine patients who are not adequately responsive to triptan drugs, ergotamine, or other analgesics (such as aspirin, acetaminophen, ibuprofen, or naproxen). Roughly 30% of patients who are suffering from severe migraine headaches, and who are treated by a specific triptan drug, do not receive adequate relief from that drug. When this occurs, other triptans are usually tested. Although a different triptan drug may help, a residual group of about 10 to 20% of all migraine patients do not respond adequately to any of the known triptan drugs. Patients who are non-responsive to triptan drugs, and patients who have numerous and frequent attacks (such as about 5 per month or more), are especially promising candidates for treatment using LT antagonists, either alone or in conjunction with a triptan drug or any other known analgesic.

Although orally ingestible formulations are generally preferred for such use, injectable formulations can also be used, especially for very severe headaches and/or in people suffering from nausea and/or vomiting, who may be unable to keep down an ingested oral formulation. Alternately, rectal suppositories, percutaneous patches, or other modes of administration can also be used by people suffering from nausea and/or vomiting.

It should be noted that the actions of leukotrienes and leukotriene antagonists tend to vary substantially, in sometimes inconsistent ways. For example, in some situations, leukotrienes cause vasoconstriction (i.e., narrowing of blood vessels), as described in Broughton-Smith 1989 and Menger 1994. But in other situations, leukotrienes appear to cause vasoconstriction, which is the opposite effect. As examples of this apparent inconsistency, the abstract of Ortiz et al 1995 opens with, "Cysteinyl-leukotrienes cause contractions and/or relaxations of human isolated pulmonary vascular preparations", and closes with, "The mechanical effects of $LTD_4$ on human pulmonary vasculature are complex and are mediated via at least two types of cysteinyl-leukotriene receptors." Similarly, the abstract of Ford-Hutchinson et al 1986 states, "[leukotrienes] may have important cardiovascular actions through mechanisms involving either vasoconstriction or indirect vasodilatation."

These apparently inconsistent and paradoxical activities of LT's seem to mirror, in some respects, certain paradoxical aspects of migraine headaches, which typically involve vasoconstriction during the early stages followed by vasodilation (which may be an overcompensating response) during the later stages. Clearly, the current state of understanding of the biochemistry and physiological effects of leukotrienes (and the medical effects of leukotriene antagonists) is nowhere near complete.

Different Types of Leukotriene Antagonists

As mentioned briefly above, LT antagonist drugs can inhibit leukotriene activity by any of at least three distinct mechanisms. One mechanism involves inhibiting the enzymes (mainly lipoxygenase enzymes) that convert arachidonic acid into leukotrienes. Drugs which inhibit biosynthesis in this manner, and which have been described in published scientific articles, include BAYx1005 (discussed in Hamilton et al 1997 and Dahlen et al 1997), MK-886 (discussed in Friedman et al 1993), MK-0591 (discussed in Diemant et al 1995), ZD2138 (discussed in Nasser et al 1994), and zileuton (also known as A-64077, discussed in Hui et al 1991 and in Knapp 1990).

A second mechanism of LT artagonism involves drugs which competitively bind to leukotriene receptors on cell surfaces, without triggering the cellular activities that are triggered by leukotrienes. Such drugs include zafirlukast, montelukast, pranlukast, BAYx7195, LY293111, ICI 204, 219, and ONO-1078, as cited above.

A third potential mechanism involves drugs which can bind to free leukotriene molecules in blood or other body fluids, thereby rendering the leukotriene molecules unable to bind to leukotriene receptors. Although the Applicant is not currently aware of any published articles describing such drugs, it is likely that (i) various such drugs have already been developed, by pharmaceutical companies that have studied leukotrienes and leukotriene antagonists, and (ii) additional drugs with that desired activity will be developed in the future, once the utility of such drugs in preventing and/or treating migraine headaches has keen publicly disclosed and recognized among migraine researchers and the pharmaceutical industry.

Accordingly, any or all of these three inhibitory pathways can be exploited, to help control and suppress leukotriene activity in patients who suffer from migraine and/or cluster headaches.

Dosages and Modes of Administration

The preferred dosages for any LT antagonist drug selected for use as disclosed herein will depend on various factors, including the age and body weight of a patient taking the medication, etc. In general, one of the primary initial goals of such drug therapy is to establish a daily oral dosage, so that a single convenient "unit dosage" formulation (usually a pill, such as a tablet, capsule, etc.) can be taken by a patient each day. The dosage levels that have already been established for the anti-asthma formulations of zafirlukast ("Accolate", which normally is taken twice a day) and montelukast ("Singulair", which normally is taken once a day) offer a good starting point for evaluating preferred dosages that will have maximum beneficial effects in preventing migraine headaches. Evaluative tests to optimize the daily dosages for various patients with particular migraine patterns or severities can be carried out using no more than routine experimentation.

It should also be noted that capsules tend to be well suited for providing a plurality of microencapsulated quantities of an LT antagonist drug. Different formulations and thicknesses for the microencapsulating material can be used, to provide an array of tiny pellets that will provide a sustained-release formulation, in a single enclosing capsule that can be taken once a day.

If desired, other types of oral formulations (such as syrups or other liquids, lozenges, troches, etc.) can be developed, and may be well-suited for patients who suffer from nausea. Various types of non-oral formulations (including injectable formulations, nasal sprays, rectal suppositories, transdermal patches, etc.) can also be developed; such non-oral formulations may be preferred for acute treatment of migraines or cluster headaches that have already commenced, especially for patients who suffer from nausea during such headaches.

As another optional approach, an LT antagonist drug can be incorporated into a single tablet, capsule, or other formulation with one or more otter drugs, to provide additive or synergistic treatment of migraines, either on a chronic preventive basis, or on an acute treatment basis.

Similarly, two or more LT antagonist drugs can be provided in a single formulation, if desired. For example, a first LT antagonist can be used which blocks a first specific type of LT receptor, and a second LT antagonist can be used which blocks a second specific type of LT receptor. Alternately or additionally, a first LT antagonist which inhibits leukotriene biosynthesis can be included in a formulation with a second LT antagonist which suppresses activity at one or more LT receptor types.

It should be noted that the currently available LT antagonist drugs, zafirlukast ("Accolate") and montelukast ("Singulair"), typically require about 4 weeks (and sometimes more) of daily oral ingestion of tablets before noticeable effects are seen in reducing the frequency of asthma attacks. However, the articles cited above, reporting the testing of various LT antagonists on asthma patients, indicate that such agents exert a variety of physiological effects within 24 hours of administration. It also should be recognized that after this new use (i.e., using LT antagonists to prevent or treat migraine and cluster headaches) is recognized and evaluated by the medical community, it is likely that formulations (including IV or intramuscular injectable formulations, nasal sprays, etc.) can be developed which will not suffer from a prolonged lag time before they become effective in reducing the frequency of migraine headaches. Such non-oral formulations can be used for any desired period of time; for example, they can be used as initial treating agents, to quickly establish a desired level of the drug in circulating blood. Subsequent used of more convenient oral tablets or capsules can be used thereafter, to sustain the desired levels of LT antagonists in the blood.

It should also be recognized that, in general, LT antagonists which function by blocking LT receptors, or by entangling free LT molecules in body fluids, may function more rapidly than agents which suppress biosynthesis of LT molecules.

Labelled Packages in Combination With LT Antagonists

This invention also discloses an article of manufacture, comprising a leukotriene antagonist drug inside a labelled package which encloses and protects the drug, wherein the labelled package indicates, to physicians and purchasers, that the leukotriene antagonist drug is effective, if taken on a daily or other chronic basis, in reducing migraine headaches (or, alternately or additionally, one or more other types of recurrent primary headache), in at least some patients who suffer from such headaches.

This type of article of manufacture, where the label is an essential element of the claimed item, and wherein the label cannot be separated, excised, or divorced from the drug contained inside the package, reflects the fact that under the laws which apply to drugs sold or human use, the drug and its labelled packaged are regarded as a single indivisible and integral item of commerce. It is illegal to sell such drugs, no matter how safe or effective they may be, unless they are packaged and labelled in a manner that has been approved by the Food and Drug Administration, in the United States (or by similar agencies in other countries).

Preferably, the drug inside the labelled package should be orally ingestible, for convenience of use. Even more preferably, the orally ingestible formulation should be a "unit dosage form", such as a tablet, capsule, or other pill which has a pre-measured quantity of the drug in each pill.

EXAMPLES

Example 1

Open-Label Trial

In a clinical trial that was organized and conducted at The New England Center for Headache (Stamford, Conn.), 17 adult patients were selected to participate. Each patient went through a 2-month baseline evaluation, followed by a 3-month trial period using daily ingestion of montelukast (a leukotriene antagonist) in tablet form.

Each patient selected for the study suffered from recurrent migraine headaches. In general, patients were selected only if they had not responded in an adequate and satisfactory manner to other treatments for migraine. Patients were not selected if they had totally failed to respond to any other preventive medications; accordingly, those who were selected generally comprised: (i) "partial responders" who were already receiving some form of preventive treatment when they entered the study, but who were still experiencing a sufficient number of migraine attacks to warrant further steps to improve their treatment; and (ii) patients who had elected not to be on other preventive medications, because of side effects such as weight gain, dry mouth, sexual dysfunction, etc. All patients who were chosen for the study, and who were informed of the drug that would be used in the study, were happy to take montelukast on a daily basis, in view of its very low level of side effects.

Each selected patient went through a 2-month "baseline" period. During that period (and also during the 3-month trial period), no medications, hormones, or other medical treatments were altered. Upon being selected, each patient was required to keep a "headache calendar" for at least two months prior to entering the trial, in order to establish baseline or "control" data which could be compared to the results of the trial period. Daily administration of montelukast, in 10 mg tablets taken once per day, began after the 2-month baseline period had been completed by a patient.

During the baseline period and the study period, the frequency, severity, and duration of migraine attacks were recorded on a calendar or log book, by each study participant. All patients who did not show a decrease of at least 50% in frequency of attacks within 2 months after commencing montelukast treatment at 1 table/day had their dosages increased to 2 tablets per day, and were evaluated 4 and 8 weeks later.

In addition, those patients who reported specific sensitivity to perfume as a migraine triggering factor were also evaluated for reduced sensitivity.

The trial was conducted as a prospective, "open label" trial. As such, blinding procedures were not used to conceal which drug a patient was taking; instead, each patient was informed of exactly what drug he or she would receive during the trial.

Within less than two months after commencing daily LT antagonist treatment, 7 of the 8 patients who were the first ones to begin the LT antagonist drug regimen reported major improvements, as indicated by decrease of at least 50% in the frequency and/or severity of migraine headaches during the trial period.

Two patients also reported a better response to triptan drugs, if and when a migraine headache did arise.

One patient who suffered from migraines triggered by perfume sensitivity reported that she had not suffered any migraine headaches triggered by perfume during the trial period.

The other 9 patients were smarted on montelukast at a later point in time, and their results are not yet available, as this is being written. However, the results from the first 8 patients who were started in the trial show quite clearly that daily ingestion of an oral LT antagonist drug can help reduce the frequency, severity, and/or duration of migraine headaches, in at least some patients.

Additional and larger trials (including double-blinded placebo-controlled trials) can be carried out, using any selected type or formulation of an LT antagonist drug, on any type, class, or group of recurrent severe headaches, as necessary to evaluate such formulation and to obtain governmental approval to label that LT antagonist drug formulation for sale as a safe and effective treatment for such headaches.

Thus, there has been shown and described a new and useful method for treating patients who suffer from recurrent severe headaches, including migraine headaches and cluster headaches. Although this invention has beer exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Boulet, L. P., et al, "Inhibitory effects of BAY x 7195, a CYS leukotriene 1 receptor antagonist, on allergen-induced asthmatic responses," *Ann Allergy Asthma Immonol* 79(2): 155–61 (1997)

Bray, M. A., et al, "Leukotriene B4: a mediator of vascular permeability," *Brit J Pharmacol* 72: 483–486 (1981)

Bray, M. A., "The pharmacology and pathophysiology of leukotriene B4," *Brit Med Bull* 39: 249–254 (1983)

Busse, W. W. "The role of leukotrienes in asthma and allergic rhinitis," *Clin Exp Allergy* 26(8): 868–79 (1996)

Dahlen, S. E., et al, "Inhibition of allergic bronchoconstriction in asthmatics by the leukotriene-antagonist ICI-204,219," *Adv Prostaglandin Thromboxane Leukotriene Res* 21A: 461–4 (1991)

Dahlen, B., et al, "Inhibition of allergen-induced airway obstruction and leukotriene generation in atopic asthmatic subjects by the leukotriene biosynthesis inhibitor BAYx 1005," *Thorax* 52(4): 342–7 (1997)

Diamant, Z., et al, "The effect of MK-0591, a novel 5-lipoxygenase activating protein inhibitor, on leukotriene biosynthesis and allergen-induced airway responses in asthmatic subjects in vivo," *J Allery Clin Immunol* 95(1 Pt 1): 42–51 (1995)

Evans, D. J., et al, "Effect of a leukotriene B4 receptor antagonist, LY293111, on allergen induced responses in asthma," *Thorax* 51(12): 1178–84 (1996)

Ford-Hutchinson, A., et al, "Biological actions of leukotrienes," *Hypertension* 8 (Part 2): II44–49 (1986)

Ford-Hutchinson, A. W., et al, "Leukotriene B4 a potent chemokinetic and aggregating substance released from polymorphonuclear leukocytes," *Nature* 286: 264–265 (1980)

Friedman, B. S., et al, "Oral leukotriene inhibitor (MK-886) blocks allergen-induced ail-way responses," *Am Rev Respir Dis* 147(4): 839–44 (1993)

Gimbrone, M. A., et al, "Leukotriene B4 stimulates polymorphonuclear leukocyte adhesion to cultured vascular endothelial cells," *J Clin Invest* 74: 1552–1555 (1984)

Hamilton, A., et al, "Pranlukast, a cysteinyl leukotriene receptor antagonist, attenuates allergen-induced early- and late-phase bronchoconstriction and airway hyperresponsiveness in asthmatic subjects," *J Allergy Clin Immunol* 102(2): 177–83 (1998)

Hamilton, A. L., et al, "Attenuation of early and late phase allergen-induced bronchoconstriction in asthmatic subjects by a 5-lipoxygenase activating protein antagonist, BAYx 1005," *Thorax* 52(4): 348–54 (1997)

Hui, K. P., et al, "Effect of a 5-lipoxygenase inhibitor on leukotriene generation and airway responses after allergen challenge in asthmatic patients,"*Thorax* 46(3): 184–9 (1991)

Knapp, H. R., "Reduced allergen-induced nasal congestion and leukotriene synthesis with an orally active 5-lipoxygenase inhibitor,"*N Engl J Med* 323(25): 1745–8 (1990)

Levine, J. D., et al, Leukotriene B4 produces hyperalgesia that is dependent of polymorpho-nuclear leukocytes" *Science* 225: 743–745 (1984)

Lewis, R. A., et al, "Meditation of local homeostasis and inflammation by leukotrienes and other mast cell dependent compounds," *Nature* 293: 103–108 (1981)

Nasser, S. M., et al, "Effect of the 5-lipoxygenase inhibitor ZD2138 on allergen-induced early and late asthmatic responses," *Thorax* 49(8): 743–8 (1994)

Ortiz, J. L., et al., "Leukotriene receptors on human pulmonary vascular endothelium," *Brit J Pharmacol* 115: 1382–86 (1995)

Piper, P. J., "Formation and action of leukotrienes," *Physiol Rev* 64: 749–761 (1984)

Roquet, A., et al, "Combined antagonism of leukotrienes and histamine produces predominant inhibition of allergen-induced early and late phase airway obstruction in asthmatics," *Am J Respir Crit Care Med* 155: 1856–63 (1997)

Smith, M. H. J., et al "Leukotriene B: a potential mediator of inflammation," *J Pharmacol* 32: 517–18 (1980)

Taniguchi, Y., et al, "The effect of an oral leukotriene antagonist, ONO-1078, on allergen-induced immediate bronchoconstriction in asthmatic subjects," *J Allergy Clin Immunol* 92: 507–12 (1993)

Taylor, I. K., et al, "Effect of cysteinyl-leukotriene receptor antagonist ICI 204.219 on allergen-induced bronchoconstriction and airway hyperreactivity in atopic subjects," *Lancet* 337(8743): 690–4 (1991)

What is claimed is:

1. A method of treating a patient who suffers from recurrent primary headaches, comprising periodic administration of at least one leukotriene receptor-blocking drug, at a dosage and frequency which is effective in reducing at least one aspect of such recurrent severe headaches in such patient.

2. The method of claim 1, wherein the patient suffers from recurrent severe headaches which are classified as migraine headaches.

3. The method of claim 2 wherein periodic administration of the leukotriene receptor-blocking drug comprises periodic ingestion of an orally-ingestible unit dosage formulation of the leukotriene receptor-blocking drug.

4. The method of claim 2 wherein the leukotriene receptor-blocking drug is selected from the group consisting of zafirlukast, montelukast, pranlukast, BAYx7195, LY293111, ICI 204,219, and ONO-1078.

5. The method of claim 2 wherein periodic administration of the leukotriene receptor-blocking drug causes a reduction in at least one aspect of such headaches selected from the group consisting of:

a. frequency of occurrence of such headaches;
   b. duration of such headaches, when they occur; and,
   c. perceived or reported severity or intensity of such headaches, when they occur.

6. The method of claim 1, wherein the patient suffers from recurrent severe headaches which are classified as cluster headaches.

7. The method of claim 6 wherein periodic administration of the leukotriene receptor-blocking drug comprises periodic ingestion of an orally-ingestible unit dosage formulation of the leukotriene receptor-blocking drug.

8. The method of claim 5 wherein the leukotriene receptor-blocking drug is selected from the group consisting of zafirlukast, montelukast, pranlukast, BAYx7195, LY293111, ICI 204,219, and ONO-1078.

9. The method of claim 6 wherein periodic administration of the leukotriene receptor-blocking drug causes a reduction in at least one aspect of such headaches selected from the group consisting of:

a. frequency of occurrence of such headaches;

b. duration of such headaches, when they occur; and, c. perceived or reported severity or intensity of such headaches, when they occur.

10. An article of manufacture comprising a leukotriene receptor-blocking drug inside a labelled package which encloses and protects the drug, wherein the leukotriene receptor-blocking drug is in an orally ingestible formulation which is effective in reducing migraine headaches in it least some patients if taken chronically, and wherein the labelled package indicates to physicians and purchasers that the leukotriene receptor-blocking drug enclosed therein is effective, when administered periodically, in reducing at least one type of recurrent primary headache in at least some patients who suffer from such headaches.

11. The article of manufacture of claim 10, wherein the orally ingestible formulation is a unit dosage form.

* * * * *